United States Patent [19]
Neveu

[11] Patent Number: 5,849,647
[45] Date of Patent: Dec. 15, 1998

[54] HYDROPHILIC COTTON LAP AND PRODUCTS MADE FROM IT

[75] Inventor: Jean-Louis Neveu, Lery, France

[73] Assignee: James River, France

[21] Appl. No.: 495,544

[22] PCT Filed: Jan. 26, 1994

[86] PCT No.: PCT/FR94/00091

§ 371 Date: Jul. 28, 1995

§ 102(e) Date: Jul. 28, 1995

[87] PCT Pub. No.: WO94/17235

PCT Pub. Date: Aug. 4, 1994

[30] Foreign Application Priority Data

Jan. 29, 1993 [FR] France ................................. 93 00928
Apr. 5, 1993 [FR] France ................................. 93 03964

[51] Int. Cl.$^6$ ............................ B32B 05/16; D04H 13/00
[52] U.S. Cl. ........................ 442/381; 442/387; 442/391; 442/392
[58] Field of Search ........................... 428/284; 442/387, 442/391, 381, 392, 160

[56] References Cited

U.S. PATENT DOCUMENTS

| | | | |
|---|---|---|---|
| 3,772,055 | 11/1973 | Anselrode | 117/38 |
| 4,018,646 | 4/1977 | Ruffo et al. | 162/146 |
| 4,647,490 | 3/1987 | Bailey et al. | 428/131 |
| 5,149,334 | 9/1992 | Lahrman et al. | 604/367 |
| 5,279,767 | 1/1994 | Phan et al. | 252/357 |
| 5,300,565 | 4/1994 | Berg et al. | 525/54.2 |
| 5,474,689 | 12/1995 | Laughlin et al. | 252/8.8 |

*Primary Examiner*—Helen Lee
*Attorney, Agent, or Firm*—Breiner & Breiner

[57] ABSTRACT

The invention relates to a hydrophilic cotton lap constituted 100% of cotton fibers. In the invention, the lap is a composite and comprises three cotton layers evincing inter-cohesiveness arising from a continuous lap manufacturing procedure. The external layers and enclosing the central layer are webs. The lap of the invention is used in the form of packaged or formatted units of hydrophilic cotton.

25 Claims, 7 Drawing Sheets

HYDROPHILIC COTTON LAP AND PRODUCTS MADE FROM IT

The invention relates to a hydrophilic cotton lap and to novel products made from it, in particular, products in the form of pattern-cut units.

The laps of the invention are 100% cotton fibers and are used to make pattern-cut or pattern-precut packaged products, such as products in the form of an accordion-pleated band packaged in a pouch and removed from the pouch as needed. This type of product is mainly used in dermatology and surgery. Moreover, the lap can be cut into napkin form or into formatted units, such as round or square pads, for uses such as makeup removal or as sanitary baby paper. Furthermore, the cut cellulose composite products made from the lap of the invention can be used as cosmetic or eye pads, or as compresses. Presently many hydrophilic cotton-based products are commercially available. Applicant itself sells hydrophilic cotton products under the trademark LOTUS for formatted-unit, precut, packaged cotton.

Regarding packaged cotton products, conventional web fabrication treats undyed baled cotton by cleaning and opening, followed by batch treatment wherein grease and wax are removed by a soda-based boiling solution to make the cotton hydrophilic. This procedure is followed by rinsing and squeezing, then bleaching, all in the batch mode, for example using oxygenated water or hydrogen peroxide. The bleached cotton, where called for, is further treated with lubricants and/or softeners (sizing). The cotton is dried before being carded to align the fibers and to form webs. A lap is formed by combining several webs previously folded in the direction of production advance to achieve a desired width. Lastly, the lap is accordion-pleated and packaged. Such a lap can be precut before being conditioned. The final product is bulky. The specific weight of a lap is about 400 to 600 $g/m^2$. The packaging takes up much space, resulting in storage problems and display difficulties when offered for sale.

The appearance of the cotton product so made is highly fuzzy. Also, the cotton product easily frays. Moreover, the precut or cut-out lap delaminates easily, the webs detaching from one another, especially in the case of cotton which is not precut.

Regarding formatted-unit cotton, the fiber treatment is the same as described above, i.e., chemical treatment and drying. Then synthetic fibers are admixed to the treated cotton in a ratio of synthetic-fibers:cotton of about 5:95 to 30:70. The synthetic fibers are heat-melting, for example, they are made of polyethylene, polypropylene or two-component fibers. They are incorporated into the cotton fibers in mixers or sizer-mixers. Next, a lap is formed on a pneumatic lapping apparatus and/or on cards. The lap then moves into a cross-flow air oven of sufficient temperature to melt the synthetic fibers. When they melt, these fibers form a binder between the cotton fibers and provide cohesion to the lap after cooling. Once cooled, the lap is cut into formatted units.

Another manufacturing procedure for a lap to make formatted products is described in French Patent Application No. 2,552,120. In this procedure, chemical boiling-off and bleaching solutions are applied to an undyed, already formed lap wound on a hollow cylinder perforated at its surface. This cylinder subsequently is placed in a collar. The treatment liquids are made to radially circulate through the turns formed by the lap inside an autoclave in such a manner that a pressure differential arises between the liquid entering the cylinder and the liquid leaving the cylinder. As a result of this pressure differential, lap cohesiveness is increased. The lap is then rinsed. Next, the lap is cut into round pad formats.

In light of the above description, cotton laps are manufactured differently depending on their use, namely, whether as a packaged product or as formatted units.

European Patent Application No. 0,405,043 describes cotton round pads comprising a central layer and at least one previously compressed external layer. Each layer corresponds to an already bleached cotton lap. Following cut-out, the layers forming the round pad are joined to one another only by their edges when the round pad is not compressed in its final state. This uncompressed product in its final state fails to offer good surface cohesiveness because the layers do not adhere to each other.

Again, presently commercially available hydrophilic cottons do not fully satisfy the consumer looking for high softness with excellent strength and resistance to delamination and excellent surface condition.

An object of the present invention is avoidance of the above noted drawbacks by creating a hydrophilic cotton lap consisting totally of cotton fibers and offering excellent cohesiveness in the absence of compressive treatment and also very high delamination resistance.

Another object of the invention is a lap of hydrophilic cotton which, while evincing excellent cohesiveness, also remains very soft to the touch.

Another object of the invention is a lap of hydrophilic cotton with a very pleasing appearance and surface condition, which will not fray at the surface and offers significantly improved fuzzing resistance relative to the products of the prior art.

Another object of the invention is a compact hydrophilic cotton lap having a substantially reduced volume as to packaging and storage.

Also, another object of the invention is a hydrophilic cotton lap used both in packaged and formatted-unit products without additional lap treatment other than pattern pre-cuts or pattern cut-outs.

Another object of the invention is novel cotton products made by pattern-cutting or pattern-precutting of the lap.

Still another object of the invention is novel cut-out, cellulose composite products based on hydrophilic cotton and comprising a lap totally consisting of cotton fibers.

In the invention, the lap of hydrophilic cotton is characterized in that it is a composite structure and comprises three cotton layers cohesive among each other on account of the continuous manufacturing process of the lap, wherein the outer layers, which are webs, enclose a central layer. In an advantageous feature of the invention, the noted webs are substantially isotropic and, preferably, are prepared using a conventional pell-mell card.

In another feature of the invention, the specific weight of each outer layer is in the range of about 5 to about 80 $g/m^2$, preferably between about 15 and 30 $g/m^2$.

In yet another feature of the invention, the central layer evinces a specific weight of between about 60 and about 400 $g/m^2$.

Other features and advantages of the invention are elucidated below in the following description relating to the attached drawings.

The lap of the invention is manufactured by a continuous method as described below.

A mixture of cotton fibers of various origins and grades is opened and cleaned. A lap with a specific weight of between 100 and 600 g/m² is formed using any appropriate mechanical means, such as a card and/or a pneumatic carder. In the present example, three layers are superposed.

The first layer is composed of a web illustratively prepared using a conventional cotton card, preferably using a conventional pell-mell card. A pell-mell card is a mechanical apparatus wherein a web can exit without requiring that the fibers are parallel in the direction of advance, i.e., are tangled-fiber webs. In this discussion, the expression "pell-mell card" covers both conventional pell-mell cards and pell-mell cards fitted with a pneumatic outlet, for example, the pell-mell cards sold by Fehrer Enterprise.

The second layer is made pneumatically, for example, on a Rando-type apparatus. Using such a machine, the fibers are projected from a toothed drum into an air flow and are sucked onto a mat or drum across which exists a partial vacuum. The fibers are randomly directed in all directions. In a practical implementation of the invention, the layer exiting this machine evinces a stratified structure. The pneumatically-deposited layer fibers are oriented substantially obliquely to the upper and lower horizontal planes of the lap.

The third layer is composed of a web similar to the first layer.

The assembly therefore constitutes a composite lap of three superposed layers, i.e., a sandwich lap.

Thereupon, this lap is moved on an endless, liquid-permeable support belt toward various treatment stations which are arrayed in a continuous line. A soda-containing boiling-off solution is gravity-poured in the form of a liquid screen transverse to the direction of advance of the lap onto the lap which thereby is impregnated with the solution. An adequate partial vacuum is generated by a suction slot located underneath the lap to allow at least a portion of the solution to cross the lap. At the same time, the amount of liquid retained by the lap is controlled by regulating the partial vacuum at the suction slot. The lap is inserted into a vaporizer and heated to about 100° C. and dwells in the vaporizer, while remaining continuous, for a given time which in particular, depends of the material flow, i.e., kg of cotton per hour.

Thereupon, the cotton is rinsed and the boiling-off liquor removed using both a second liquid screen and a partial-vacuum slot associated with an average partial vacuum.

The boiled-off, hydrophilic lap is impregnated with a bleaching solution, illustratively containing chlorite, sodium hypochlorite or preferably oxygenated water, in the same manner as with the boiling-off solution. Thereupon, the lap is introduced into a vaporizer and heated to about 100° C. in order to carry out effective bleaching.

Next, the lap is rinsed by a sequence of liquid screens associated with suction slots.

This lap treatment provides adhesion between its constituent layers and excellent overall cohesiveness without the need for additional mechanical or chemical treatment, such as compression.

Following drying, the lap can be used directly in the preparation of formatted units or packaged hydrophilic cotton. This processing stage implies cut-out operation(s) using an alternating press or a rotary tool.

Figure 1:
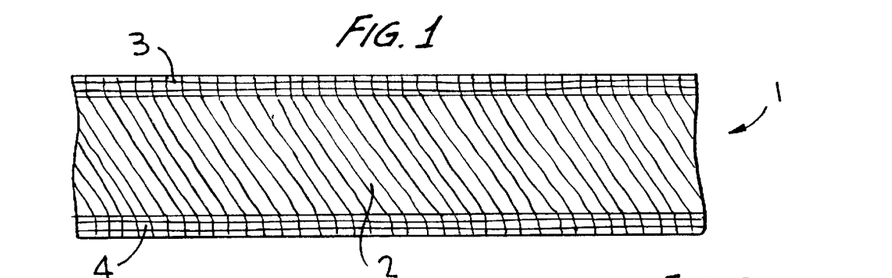
FIG. 1 is a schematic cross-section of a hydrophilic cotton lap of the invention.

As shown in FIG. 1, the hydrophilic cotton lap 1, which is composed 100% of cotton, comprises three layers, namely a central layer 2 and two external or surface layers 3 and 4 enclosing central layer 2.

Central layer 2 is thicker. Its specific weight varies between about 60 and about 400 g/m². When the specific weight of the central layer is close to the lower limit of this range, for example 150 g/m², the lap is compact and preferably used for a formatted unit cotton product. When the specific weight of the central layer is closer to the upper limit of the range, the lap preferably is used for a bulkier, packaged cotton product. The central layer is characterized by stratified cotton fibers which are oriented substantially obliquely between the two planes formed by the external layers. This fiber orientation results from the pneumatic preparation of the central layer using a Rando-type apparatus.

The surface or external layers 3 and 4 are webs made on a pell-mell card. Each external layer evinces a specific weight of between about 5 and about 80 g/m², preferably between 15 and 30 g/m². These webs are two-dimensional and substantially isotropic in their plane of formation. They comprise fibers simultaneously oriented in the direction of advance and in the transverse direction. The cotton fibers for the webs are selected from among attractive and long fibers. The layers 3 and 4 impart an exceptional surface condition to the lap. The lap is fuzz-free and does not fray in comparison with the 100% cotton products currently on the market because of the surface fiber orientations in two orthogonal directions or in an isotropic manner. The webs form a mask relative to the fibers of the central layer and retain the fibers of the central layer. As a result, when in use, for example against the skin, the hydrophilic cotton products of the invention do not come apart and hence do not leave fibers sticking to the skin.

Next, the lap is precut or cut into the shape of a round, square, rectangular, or any other regular polygonal shaped pad. The cotton products so made further differ from the cut products of the prior art, in particular, by being crimped during this cutout procedure which is carried out in a punch press, an alternating or rotary mechanical cutter, or any other machine bringing the layers closer together in the cutting zone.

The expression "alternating apparatus" is used below to denote a mechanical, alternating cutting tool or machine.

Similarly, the expression "rotary apparatus" is used below to denote a mechanical, rotary cutting machine or tool.

Figure 2:
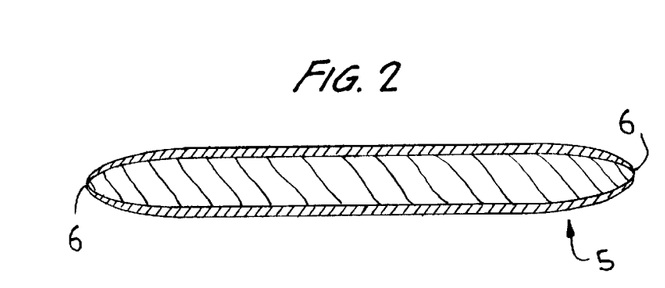
FIG. 2 schematically shows a cross-section of a cut-out cotton product of the invention, such as a round pad.

As shown in FIG. 2, the cut cotton product, in this instance round pad 5, comprises two edges 6 of lesser thickness, in this case about 0.2 mm, whereas the thickness at the round pad center is about 1.5 mm or more. At its periphery, the cut cotton product comprises a sealed envelope corresponding to the two interconnected surface layers 3 and 4. This peripheral cohesion reinforces the already extant surface cohesiveness between the central layer 2 and each of the external layers 3 and 4. Such a crimped product can be sliced without risking delamination and offers a better appearance.

Be it also borne in mind that the manufacture of the lap of the invention does not require sizing.

Figure 3:
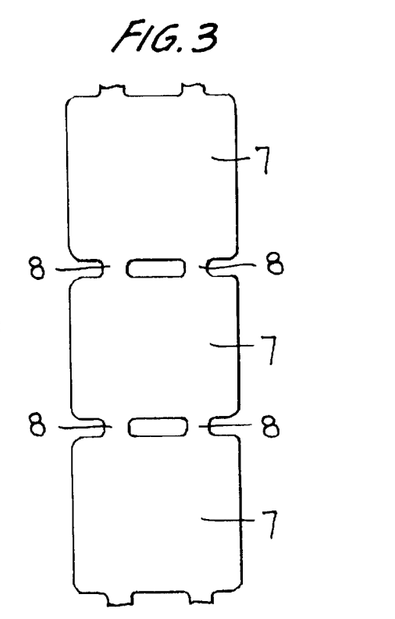
FIG. 3 shows a series of precut cotton squares linked by attachment sites.

Formatted or packaged products can be precut in such a way as to retain attachment sites between the different formatted units or rectangles of a packaged cotton band. This novel product is illustrated in FIG. 3. The various formatted units, shown square in this case, are interconnected by easily ruptured attachment sites 8. The interconnected formatted units can be packaged in the form of accordion-folded bands. The manufacture of this interconnected product is simpler and quicker than for formatted-unit products.

The novel cotton lap of the invention offers many advantages with some unexpected features. Some lap properties, or properties of products made from this lap, are measured and compared with the properties of prior art products.

More specifically, on one hand a lap I of the invention is prepared, bleached and cut into bands, and on the other hand a control lap A is made. Control lap A is 100% cotton with fibers treated in a conventional chemical manner. This control lap is prepared by carding staple fibers.

These different laps, namely lap I of the invention and control lap A, are cut into 50×100 mm formatted units interlinked by attachment sites.

Also, 100% cotton round pads as commercially sold in the marketplace are used. These round pads are referred to below as control pads B.

In each of the following tests, measurements are taken on 5 product samples (lap, formatted units or round pads) of the invention and on 5 control samples. The listed test values are the averages.

Lap Characteristics

The following were measured for each lap:

specific weight, thickness at a pressure of 20 g/m² applied to the lap, and the bulk of the lap thickness absent any significant pressure applied to it (rigorously, a very low pressure of 2 g/m² is applied).

The apparent density is calculated from the ratio of specific weight to bulk.

The table below shows the test results:

|   | specific weight g/m2 | thickness mm | bulk mm | apparent density kg/m³ |
|---|---|---|---|---|
| I | 232 | 2.5–3.0 | 4 | 55 |
| A | 434 | 5 | 8 | 54 |

This table shows that the apparent densities of the two kinds of laps are virtually identical.

Apparent Density of Rounds Pads

The apparent density is measured on one hand for round pads made by cutting the lap of the invention on an alternating apparatus and on the other hand for control round pads B.

The values listed in the table below relate to equivalent specific weights of the round pads.

|   | Apparent density kg/m³ |
|---|---|
| I | 65 |
| B | 49 |

The tests show that the cut round pads of the invention are much more compact than the control pads B. This phenomenon can be explained by the crimping which enhances product compactness relative to conventional uncrimped products, in this instance control pad B. These more compact products are popular with the user.

Also, the lap is highly compact and its density increases, i.e., at constant mass, the lap volume decreases. These products are much more compact than conventional ones. Consequently, considerable space is saved both in the packages and in storage and displays. The volume reduction is about 25% or more. Illustratively, the cotton packages are shallower.

Separating the Precut Formatted Units

The formatted units precut on alternating or rotary apparatus are linked to each other by attachment sites. In this case, the force required to separate two formatted units from each other, that is to rupture them apart, is measured. This force is stated in Newtons (N).

The test is run on a dynamometer, more specifically on a commercial instrument called Instron. The test parameters are as follows:

Instron speed=100 mm/min gap between the Instron jaws=50 mm, and test-pan width=95 mm.

The table below lists the test results.

|   | Force of separation (N) | Force for 100 g/m² (N) |
|---|---|---|
| I | 12 | 5.17 |
| A | 7 | 1.61 |

Accordingly, the force required to separate two formatted units is much larger when the units are produced from the lap of the invention even though it is much more lightweight. This feature is completely surprising. Thus, the product is warp-resistant. The formatted units can be detached from each other by pulling harder on them while nevertheless retaining an undeformed product, i.e., a formatted unit ready for use.

Lap Tear-Strength

The tear-strength (Ts) in Newtons of each lap is measured in the direction of advance and in the transverse direction using commercial Instron test equipment by pulling on the lap until rupture. The tear-strength is expressed in Newtons (N).

The test parameters are as follows:

Instron apparatus speed=100 mm/min test-pan width=100 mm, and gap between the Instron jaws=25 mm.

The table below lists the results.

|   | Ts in direction of advance (N) | Ts in direction of advance at 100 g/m² (N) | Ts in transverse direction (N) | Ts in transverse direction at 100 g/m² (N) |
|---|---|---|---|---|
| I | 32 | 13.8 | 7.6 | 1.75 |
| A | 49 | 11.3 | 1.03 | 0.24 |

It follows from the above table that the tear strength in the direction of advance and at 100 g/m² surprisingly is larger for the lap of the invention. The strength increase in the transverse direction is even more pronounced. The product, therefore, is stronger and has a longer life. The transverse tear strength can be explained by the method used in the present invention, i.e., the lap being pneumatically formed on Rando-type apparatus, and the fibers oriented two- and even three-dimensionally. Some fibers are oriented diagonally relative to the direction of advance.

The procedures employed in the manufacture of the prior art laps result in laps with parallel fibers and lack any inter-fiber bonding. Consequently, these prior art laps suffer from very poor transverse strength.

Delamination of the Lap and of Products of the Invention

In this test, the delamination strength of a lap neither cut nor precut is compared with that of a product, more specifically a round pad, which was cut on an alternating apparatus. These products differ from each other in that the lap evinces uncrimped edges while the round pads evince crimped edges, as shown in FIG. 2, as a result of cutting.

Instron apparatus was used for this testing. The test parameters were as follows:

Instron apparatus speed=20 mm/min,
test-pan width=50 mm, and
gap between the jaws=50 mm.
The specific weight of the tested laps was 200 g/m².
Stated in centi-newtons (cN), the delamination strengths found were as follows:

|   | strength of uncrimped lap (cN) | strength of crimped round pad (cN) |
|---|---|---|
| I | 10 | 12 |

It is noted that prior to any crimping, the lap already offers good delamination strength due to the interbonding of the layers resulting from its continuous manufacture.

In view of the steps discussed above, crimping further improves the delamination strength. This bonding by crimping in the case of the lap of the invention arises only when it has been kept free of any sizing and leads to unexpected results.

Illustratively, on account of the inter-layer cohesiveness resulting from the specific physical and chemical treatments in the manufacturing of the cotton lap and further by the crimping ensuing from its cutting step, products having surprising delamination strengths can be made. Round cotton pads of this kind, when packaged into a pouch, then are well distinct from one another when pulled out of the pouch. And when in use, they will not separate into several layers the way conventional products do.

In spite of high cohesiveness and high compactness, these products retain great softness in use.

Other Features

The lap and products of the invention offer wholly satisfactory equilibria between absorption and tear strength. The number of knots (neps) in the lap of the invention is low as compared with heretofore known products.

Fuzz Resistance

This resistance is measured by the pilling test for the fuzz in products of the invention and for products presently on the market.

The testing is carried out on cut round pads. The testing consists in applying an adhesive tape to a round pad's surface, pulling the tape and comparing the quantity of fibers which are pulled off the product.

Little fuzz is created in the products of the invention as compared with the other products. This feature can be attributed to the apparent product density which is larger in the case of the invention. As a result, the product appearance is improved and is excellent. The finish and life of the product also are largely enhanced when the products of the invention are used.

Certain features of the lap and of products made from it, based on their processing as mentioned in the above description, also were observed and compared with prior art products on the basis of the microphotographs shown in the drawing.

The prior art products are illustrated on one hand by control round pads B made of 100% cotton, and on the other hand by control round pads C made from a cotton lap comprising bonded synthetic fibers which impart some cohesiveness to the lap.

The various round-pad photos were taken with an electron microscope.

FIGS. 4a–4b and 7a–7b correspond to edge views of each round pad.

FIGS. 5a–5b, 8a–8b and 10 correspond to cross-sections of the middle of each round pad.

Figure 6:
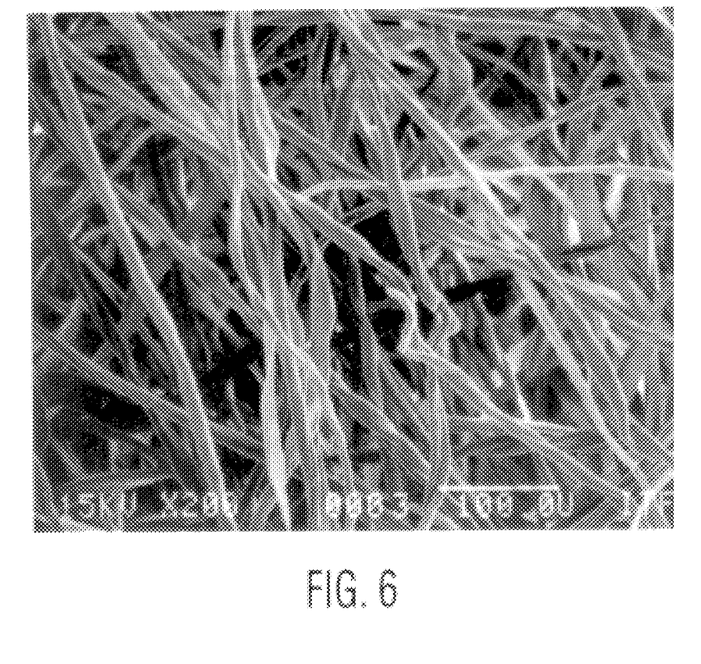
FIG. 6 is a microphotograph of one of the surfaces of the round pad of the invention shown enlarged to 200×.
Figure 9:
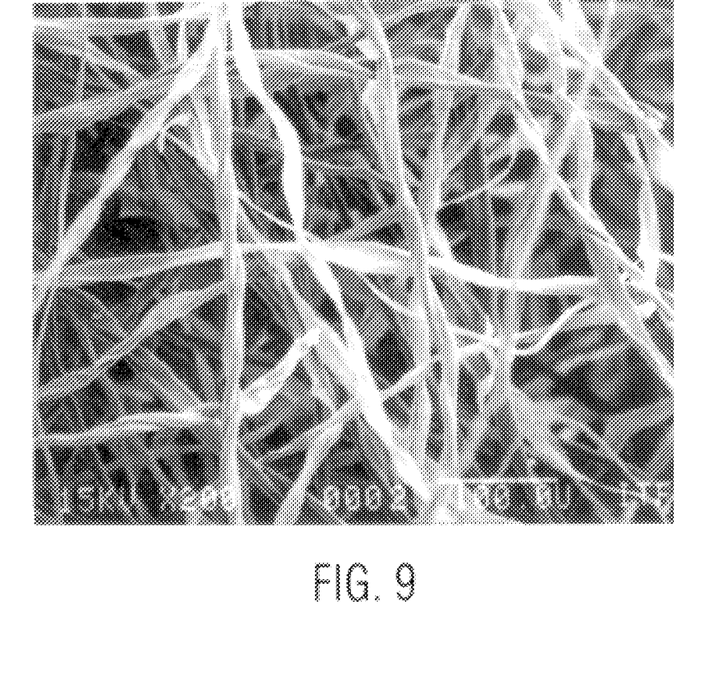
FIG. 9 is a microphotograph of a surface of control round pad B shown enlarged at 200×.
Figure 11:
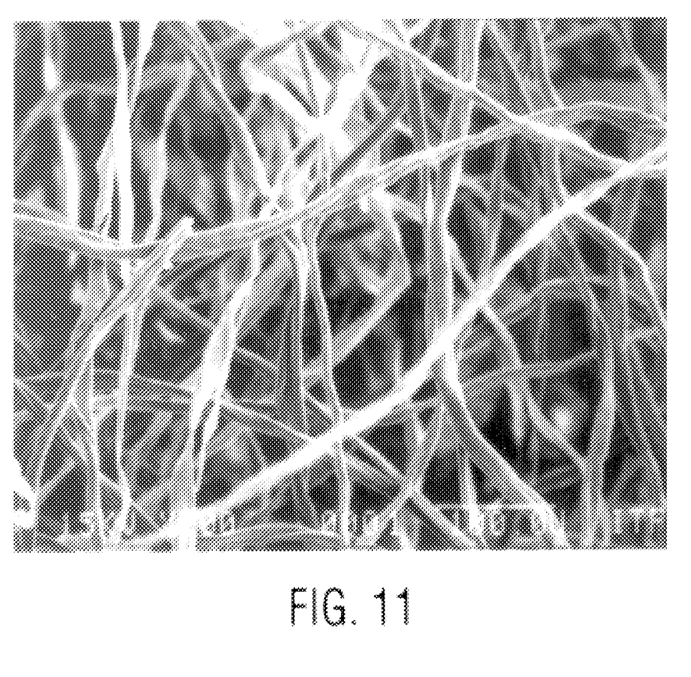
FIG. 11 is a microphotograph of a surface of control round pad C shown enlarged at 200×.

FIGS. 6, 9 and 11 correspond to surface views of the round pads.

Figure 4A:
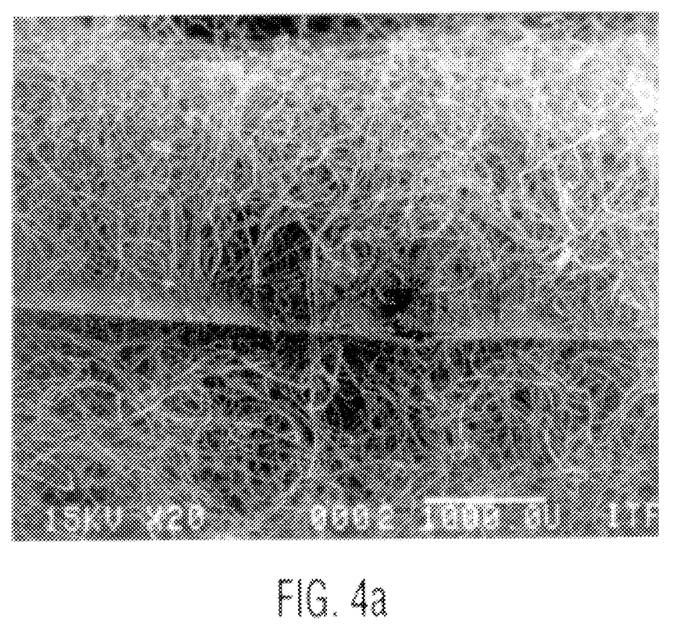
FIGS. 4a and 4b are microphotographs of an edge of a cotton round pad of the invention shown in an enlargement of 20× and 200×, respectively.

The photograph of FIG. 4a clearly shows a well defined horizontal crimping line made by cutting on an alternating apparatus. The products of the invention evince very thin edges bounded by this crimping line.

Figure 4B:
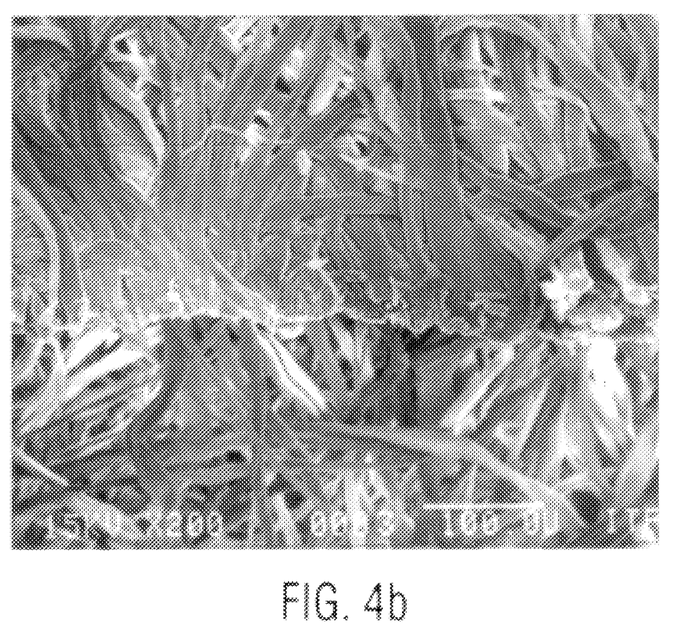

FIG. 4b shows the inter-welding of the cotton fibers. This effect is achieved by cutting the round pad on an alternating apparatus.

Figure 7A:
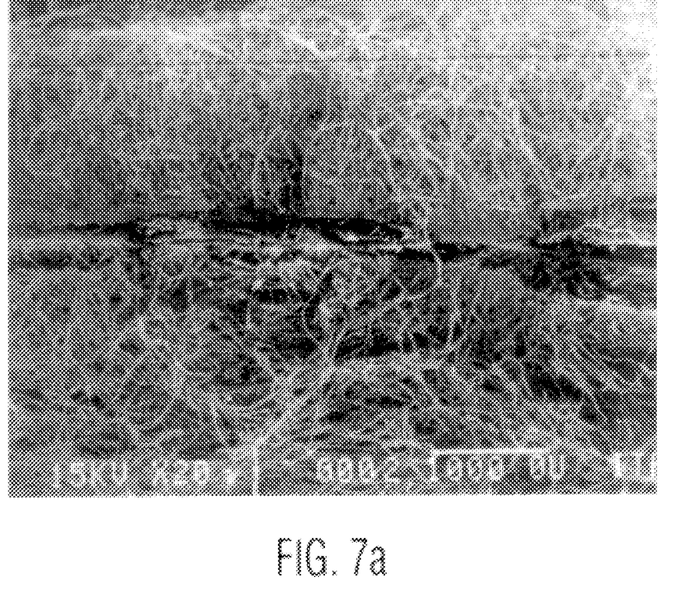
FIGS. 7a and 7b are microphotographs of the edge of control round pad B as commerically available, made of 100% cotton shown enlarged, respectively, at 20× and 200×.
Figure 7B:
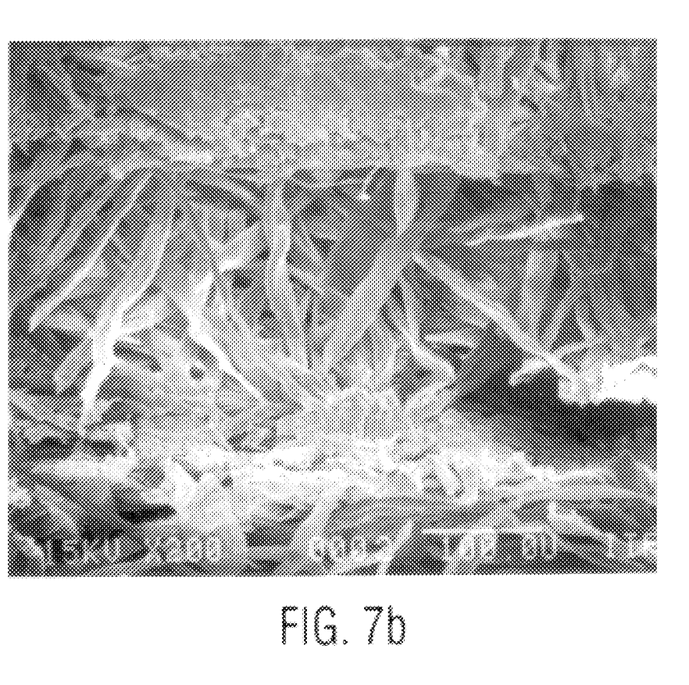
Figure 8A:
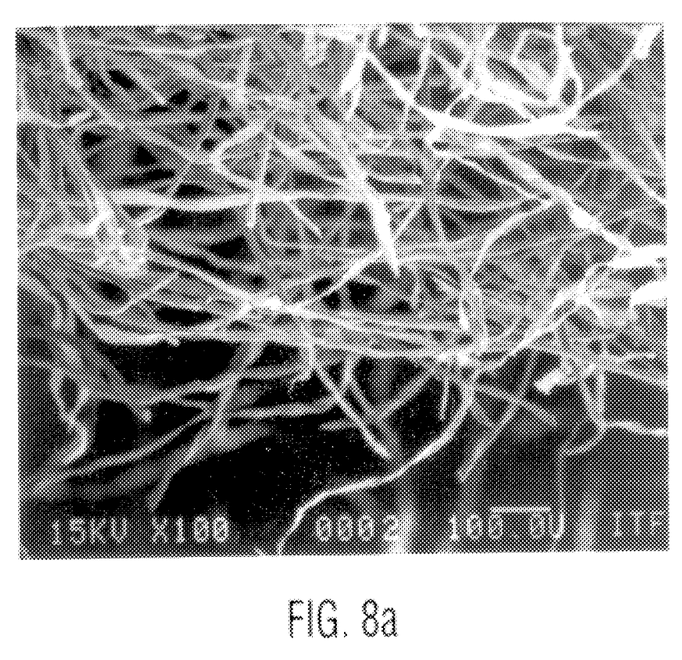
FIGS. 8a and 8b are microphotographs of control round pad B at each of its surfaces shown enlarged, respectively 100× and 66×.
Figure 8B:
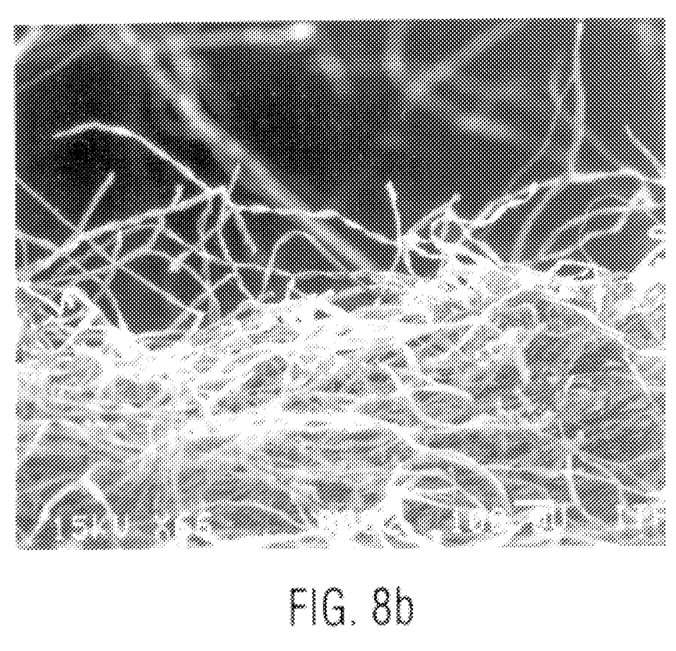

As a comparison, control round pad B shown in FIG. 7a comprises several irregular and discontinuous lines near the edge of the round pad. There is no single, well-defined crimping line. A multiple effect is present instead. Photo 7b in turn shows that the fibers are not interbonded.

As regards control round pad C, no edge photo is shown because of the lack of crimping.

Figure 5A:
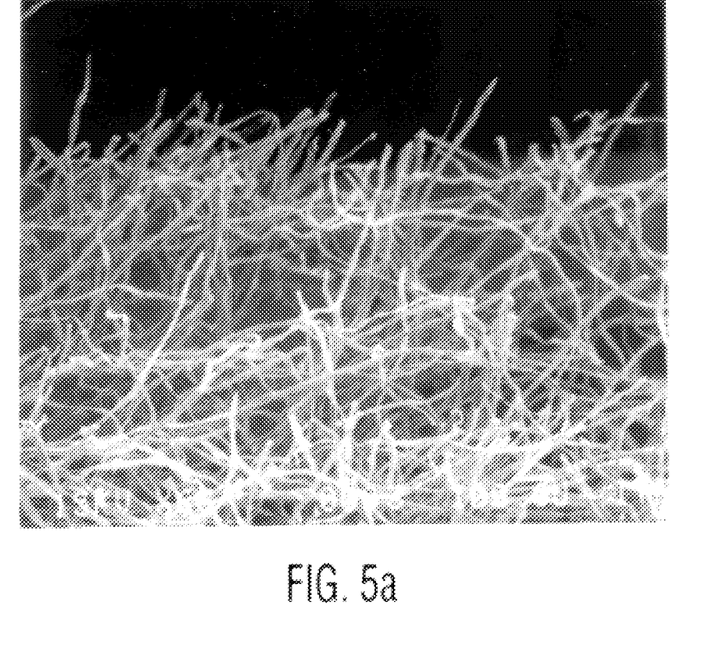
FIGS. 5a and 5b are microphotographs of a cross-section of a round pad of the invention respectively near each round pad face and shown at an enlargement of 66×.
Figure 5B:
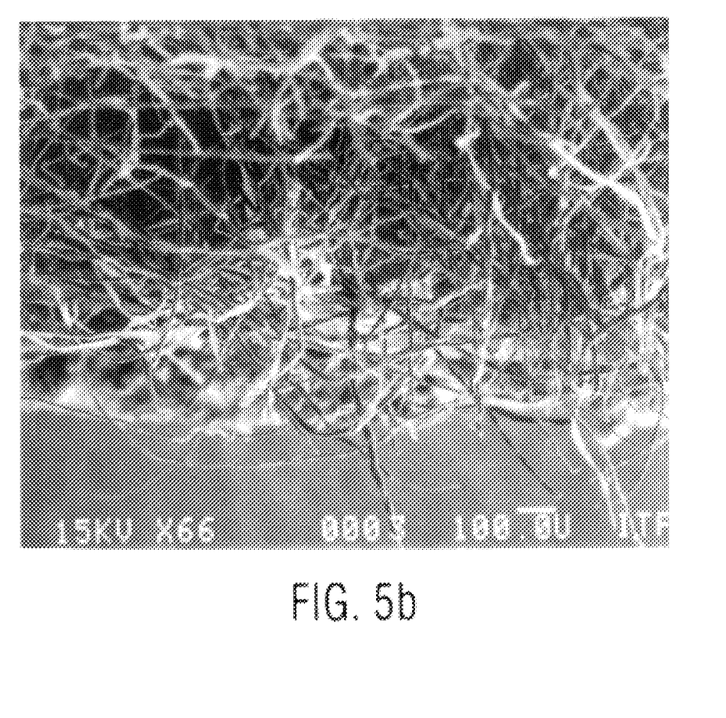

FIGS. 5a–5b and 8a–8b, respectively, correspond to cross-sections of round pads of the lap of the invention and control round pads B. The fibers are oriented in three dimensions. In the case of the invention, this fiber orientation arises from forming the lap on a pneumatic lapping machine. More specifically, this three-dimensional fiber distribution is shown in FIG. 5b. Moreover, the lower part of this cross-section shows a central zone with fibers clearly defined in it and two more blurred zones on either side of this central zone wherein the fibers are present in a plane to the rear of that in the photographed cross-section. This feature illustrates the grid effect imparted to the fibers, in this instance by the drier cloth or mat on one surface of the round pad.

Figure 10:
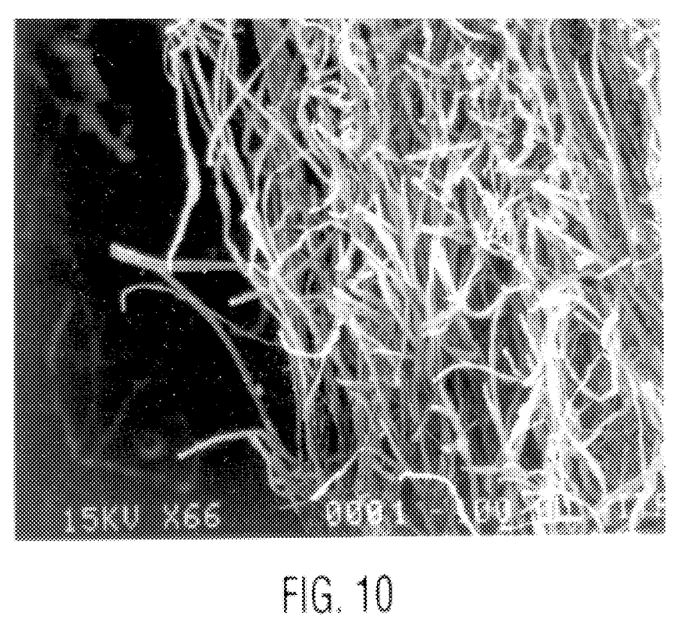
FIG. 10 is a microphotograph of a cross-section of another control round pad C made from a lap comprising synthetic fibers and shown enlarged at 66×.

FIG. 10 shows a cross-section of control round pad C and illustrates the two-dimensional distribution of the fibers resulting from the webs and their superposition in the lap. FIG. 10 furthermore shows the presence of round and smooth fibers which are synthetic bonding fibers in control round pad C.

FIG. 6 is a photo of a surface of the round pad of the invention and shows the regular and balanced distribution of the fibers.

The surfaces of the control round pads B and C, respectively illustrated by the microphotographs of FIGS. 9 and 11, are more irregular. FIG. 9 furthermore shows the presence of many "dead cotton" fibers corresponding to very fine fibers and FIG. 11 shows the presence of synthetic fibers.

The round pads of the invention shown in the microphotographs as a rule offer a pleasant finished appearance when compared with the round pads of the prior art.

The invention furthermore relates to formatted products made by cutting or precutting at least two laps of the invention such as described above. These products are thicker and illustratively are round pads comprising two laps bonded to each other by crimping their edges. In this case, the laps are cut, preferably on a rotary apparatus, such apparatus inherently improving the crimping between the laps.

Another object of the invention are composite products of formatted units and made of hydrophilic cotton comprising one lap consisting of 100% cotton fibers itself comprising three layers as described above, and at least one fourth external layer composed of at least in part cellulose fibers and located on one side of the above described three-layer lap. This composite product of formatted units is crimped during cutting on a rotary cutter. The supplementary external layer(s) is(are) unsized.

The formatted-unit products can be cut into the form of a round, square, rectangular, or any other regular polygonal-shaped pad.

Figure 12:
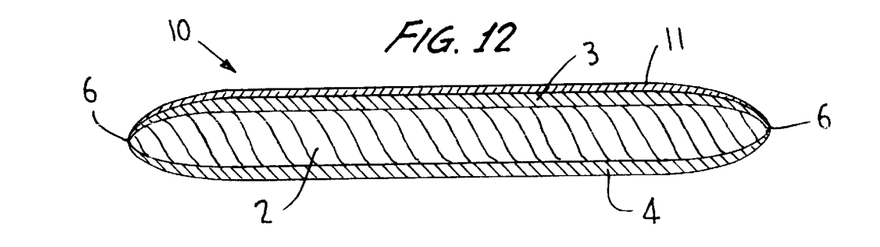
FIG. 12 is a schematic cross-section of a composite formatted product of the invention cut into the shape of a round pad.
Figure 13:
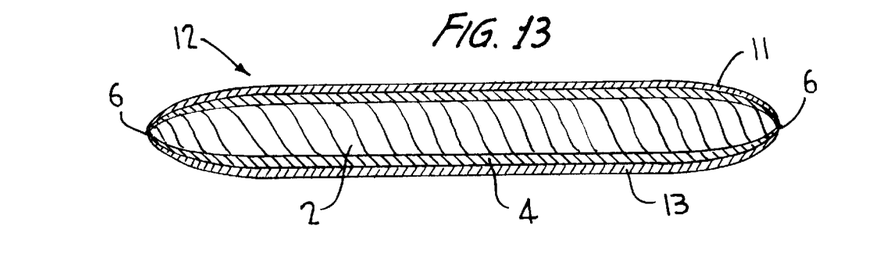
FIG. 13 is another schematic cross-section of a composite formatted product of the invention cut into the shape of a round pad.

FIGS. 12 and 13 illustrate this composite product of formatted units and is shown therein as a cut-out formatted unit and more particularly as a round pad.

According to FIG. 12, the formatted unit or round pad 10 comprises a 100% cotton fiber lap composed of central layer 2, two external layers 3 and 4, and an unsized external layer 11 constituted of cellulose fibers and located on external layer 3. The formatted unit or composite round pad, made by cutting on a rotary cutter, comprises edges 6 of reduced thickness. Surprisingly, crimping is excellent.

As shown in FIG. 13, the formatted unit or round pad 12 moreover includes a fifth external layer 13 located on outer layer 4 of the lap constituted of 100% cotton fibers. Layers 11 and 13 can be the same or different materials.

The cellulose fibers composing at least part of the material of the external layers illustratively are paper fibers or also textile fibers partly of natural or synthetic origins.

Accordingly, a composite product of formatted units can comprise an absorbing surface corresponding to a 100% hydrophilic cotton external lap layer and a less absorbent or impermeable protecting surface corresponding to the external layer. Illustratively, the latter consists of a layer of tissue paper or cellulose wadding or also of a plasticized layer of paper.

Moreover, the external product layer or the composite formatted unit can be a non-woven bonded by an adhesive or it can be thermally bonded or be bonded by means of water jets. This non-woven must contain at least in part cellulose, textile fibers such as viscose, cotton, or other fibers.

These composite cotton products in the form of formatted units can be used to apply cosmetic or pharmaceutical products in the form of creams, ointments or gels to the skin such that the fingers holding the formatted unit do not come into contact with the applied product when being used.

Other composite products in the form of formatted units can remain totally absorbent and comprise one or two external layers placed on the 100% cotton lap of three layers, the external layers being composed of a woven textile, such as gauze. Such products are useful as compresses, for example to treat wounds.

The composite products are manufactured on rotary cutting apparatus. Pilot runs were manufactured using a commercial FALU® machine made by K. FASSBIND-LUDWIG AND CO. AG. This machine is composed of cylindrical tool bearing cutters or knives corresponding to a desired cutting pattern and is applied against a smooth surface of a roller to carry out the cutting into the desired pattern. Upstream of the cutting stage, another cylinder can be provided for calendering and hot or cold embossing which makes contact with the cylindrical tool in order to apply patterns to the lap fed to the cylindrical tool. The lap and the external layer(s) are supplied superposed at that site. At the time of cutting, the external layer(s), constituted at least in part of cellulose fibers different from the layers forming the 100% cotton lap, bond(s) to the lap by its (their) periphery(ies). The finished products evince a well defined crimping line. This mechanical linkage of the edges arises from the cellulose nature of the fibers which compose at least in part the external layer(s) and the cotton lap and because these fibers or the materials forming the lap and the external layers are unsized.

On an industrial scale, a rotary apparatus of the kind sold by SCHOBER is used for pattern cutting.

The delamination strength of composite products in the form of round pads cut on the FALU® machine described above was measured.

A round pad of the invention, namely E, was made composed of 100% cotton, not a composite, and evincing a specific weight of 200 g/m$^2$. Additionally, composite round pads made from lap forming a 100% cotton round pad as described above were made. The composite round pads F, G and H comprise an external layer respectively constituted of a foil of paper or tissue, a foil of cotton gauze, and a non-woven foil comprising cotton and viscose fibers, and having a specific weight of 60 g/m$^2$.

The procedure for measuring the delamination strength is as follows:

- an adhesive tape is symmetrically applied to each of the round pad's surfaces, the adhesive tape projecting beyond each round pad surface,
- each projecting adhesive tape of each round pad surface is placed between the jaws of a dynamometer, and
- the force required to separate the layers is measured.

The results listed in the table below are ranges of values measured on several 100% cotton round pads of the invention and on composite round pads F through H. The delamination strength is stated in centi-newtons (cN).

| Round pads | E | F | G | H |
| --- | --- | --- | --- | --- |
| Force (cN) | 10 to 15 | 20 to 30 | 15 to 20 | 15 to 25 |

The above table shows that the composite round pads evince unexpected delamination strength which is highly improved over a round pad of the invention that is not a composite and that also was made by cutting with a rotary apparatus.

These new products offer an especially well-finished appearance and make it possible for the user to handle them on an external surface which is made of a material different from that of the cotton lap which is the absorbing surface.

The invention also covers all equivalent or supplementary means within the knowledge of one skilled in the art and omitted from the above description.

I claim:

1. A hydrophilic cotton lap composed 100% of cotton fibers, the lap comprising:

three cohesive cotton layers, said layers being a first external cotton layer forming a plane, a second external cotton layer forming a plane, and a central cotton layer positioned between said first external cotton layer and said second cotton layer, wherein said first external cotton layer and said second external cotton layer are carded webs, and said central cotton layer comprises stratified cotton fibers oriented in a substantially oblique manner between said planes formed by said first external cotton layer and said second external cotton layer.

2. Hydrophilic cotton lap according to claim 1 wherein said first external cotton layer and said second external cotton layer are substantially isotropic.

3. Hydrophilic cotton lap according to claim 2 wherein each said web is made using a pell-mell card.

4. Hydrophilic cotton lap according to claim 1 wherein said central cotton layer is formed using pneumatically deposited fibers.

5. Hydrophilic cotton lap according to claim 1 wherein said first external cotton layer and said second external cotton layer each have a specific weight in a range of from about 5–80 g/m$^2$.

6. Hydrophilic cotton lap according to claim 1 wherein said first external cotton layer and said second external cotton layer each have a specific weight in a range of from about 15–30 g/m$^2$.

7. Hydrophilic cotton lap according to claim 1 wherein said central cotton layer has a specific weight in a range of between from about 60–400 g/m$^2$.

8. Hydrophilic cotton lap according to claim 1 wherein said lap, following cutting and crimping of said lap, has an edge thickness of about 0.2 mm and a mid-portion thickness of about 2 mm.

9. Hydrophilic cotton lap according to claim 1 wherein said lap is free of sizing.

10. Hydrophilic cotton product in packaged form comprising at least one of said hydrophilic cotton lap of claim 1 following pattern-cutting or pattern-precutting of said at least one of said hydrophilic cotton lap.

11. Hydrophilic cotton product in formatted units comprising at least one hydrophilic cotton lap of claim 1 following pattern-cutting or pattern-precutting of said at least one of said hydrophilic cotton lap.

12. Hydrophilic cotton product according to claim 11 wherein said product has a shape selected from the group consisting of round, square, rectangular and other regular polygonal shapes.

13. Hydrophilic cotton product according to claim 11 wherein said lap is pattern-precut so that said formatted units are linked by attachment sites.

14. A hydrophilic cotton product in formatted units composed substantially of cotton fibers, the product comprising:

three cohesive cotton layers, said layers being a first cotton layer forming a plane, a second cotton layer forming a plane, and a central cotton layer positioned between said first cotton layer and said second cotton layer; and at least one external layer, said at least one external layer being disposed about said first cotton layer, wherein said at least one external layer is formed in part by cellulose fibers, and wherein said first cotton layer and said second cotton layer are each a carded web, and said central cotton layer comprises stratified cotton fibers oriented in a substantially oblique manner between said planes formed by said first cotton layer and said second cotton layer.

15. Hydrophilic cotton product according to claim 14 wherein said at least one external layer is unsized.

16. Hydrophilic cotton product according to claim 14 wherein said product is crimped and formed by pattern-cutting using a rotary mechanical cutter.

17. Hydrophilic cotton product according to claim 14 wherein said product has a shape selected from the group consisting of round, square, rectangular and other regular polygonal shapes.

18. Hydrophilic cotton product according to claim 14 wherein said product has an embossed pattern.

19. Hydrophilic cotton product according to claim 14 wherein said at least one external layer is a cellulose fiber-based woven or non-woven material.

20. Hydrophilic cotton product according to claim 19 wherein said at least one external layer is a layer of gauze.

21. Hydrophilic cotton product according to claim 14 wherein said at least one external layer is a non-woven foil.

22. Hydrophilic cotton product according to claim 14 wherein said at least one external layer is a paper foil which optionally is plasticized.

23. A hydrophilic cotton product in formatted units composed substantially of cotton fibers, the product comprising:

three cohesive cotton layers, said layers being a first cotton layer forming a plane, a second cotton layer forming a plane, and a central cotton layer positioned between said first cotton layer and said second cotton layer; and at least two external layers wherein a first external layer is disposed about said first cotton layer and a second external layer is disposed about the second cotton layer, and wherein each of said at least two external layers are formed in part by cellulose fibers, and wherein said first cotton layer and said second cotton layer are each a carded web, and wherein said central cotton layer comprises stratified cotton fibers oriented in a substantially oblique manner between said planes formed by said first cotton layer and said second cotton layer.

24. Hydrophilic cotton product according to claim 23 wherein said at least two external layers are unsized.

25. Hydrophilic cotton product according to claim 23 wherein said at least two external layers are gauze layers.

* * * * *